(12) United States Patent
Kord

(10) Patent No.: US 11,806,129 B2
(45) Date of Patent: Nov. 7, 2023

(54) CALIBRATION OF AN INERTIAL MEASUREMENT UNIT FOR IMPROVING THE ACCURACY OF A BIOMECHANICAL SKELETON

(71) Applicant: Ali Kord, Lewes (GB)

(72) Inventor: Ali Kord, Lewes (GB)

( * ) Notice: Subject to any disclaimer, the term of this patent is extended or adjusted under 35 U.S.C. 154(b) by 312 days.

(21) Appl. No.: 16/352,096

(22) Filed: Mar. 13, 2019

(65) Prior Publication Data

US 2019/0282126 A1 Sep. 19, 2019

Related U.S. Application Data

(60) Provisional application No. 62/642,424, filed on Mar. 13, 2018.

(51) Int. Cl.
*A61B 5/107* (2006.01)
*A61B 5/11* (2006.01)
*A61B 5/00* (2006.01)

(52) U.S. Cl.
CPC .......... *A61B 5/1072* (2013.01); *A61B 5/1073* (2013.01); *A61B 5/1121* (2013.01); *A61B 5/1126* (2013.01); *A61B 5/1107* (2013.01); *A61B 5/486* (2013.01); *A61B 2562/0219* (2013.01)

(58) Field of Classification Search
CPC ... A61B 5/1072; A61B 5/1126; A61B 5/1121; A61B 5/1073; A61B 5/486; A61B 5/1107; A61B 2562/0219; A61B 5/702; A61B 2560/0223
See application file for complete search history.

(56) References Cited

U.S. PATENT DOCUMENTS

| | | | |
|---|---|---|---|
| 1,220,476 A | 3/1917 | Ujdur | |
| 2,146,799 A | 4/1939 | Davis, Jr. | |
| 3,576,537 A * | 4/1971 | Ernst | G07C 9/25 235/380 |
| 3,576,538 A * | 4/1971 | Miller | G07C 9/257 235/380 |
| 3,668,633 A * | 6/1972 | Sadowsky | G06K 9/00013 382/126 |
| 4,173,074 A | 11/1979 | Newman | |
| 4,357,597 A * | 11/1982 | Butler | A61B 5/1171 382/115 |
| 4,897,924 A | 2/1990 | Tepley | |
| 5,140,998 A | 8/1992 | Vickers | |
| 6,165,148 A | 12/2000 | Carr-Stock | |
| 6,561,995 B1 | 5/2003 | Thibodo, Jr. | |
| 2005/0083297 A1* | 4/2005 | Duncan | A63F 13/245 345/156 |
| 2005/0101897 A1 | 5/2005 | Froom | |
| 2013/0230135 A1* | 9/2013 | Hoshino | A61B 6/04 378/36 |

* cited by examiner

*Primary Examiner* — Rene T Towa

(74) *Attorney, Agent, or Firm* — GSS Law Group; Gregory S. Smith; Phillip M. Wagner

(57) ABSTRACT

A calibration fixture provides a repeatably accurate tool for measuring offset angles between measurement axes for inertial measurement units (IMUs) used in motion capture. The measured offset angles may be used to correct angles measured by the IMUs to create a biomechanical skeleton that accurately represents movements of a motion capture subject. The disclosed embodiments are applied segments of a biomechanical skeleton providing a mathematical model of a human arm and hand.

3 Claims, 5 Drawing Sheets

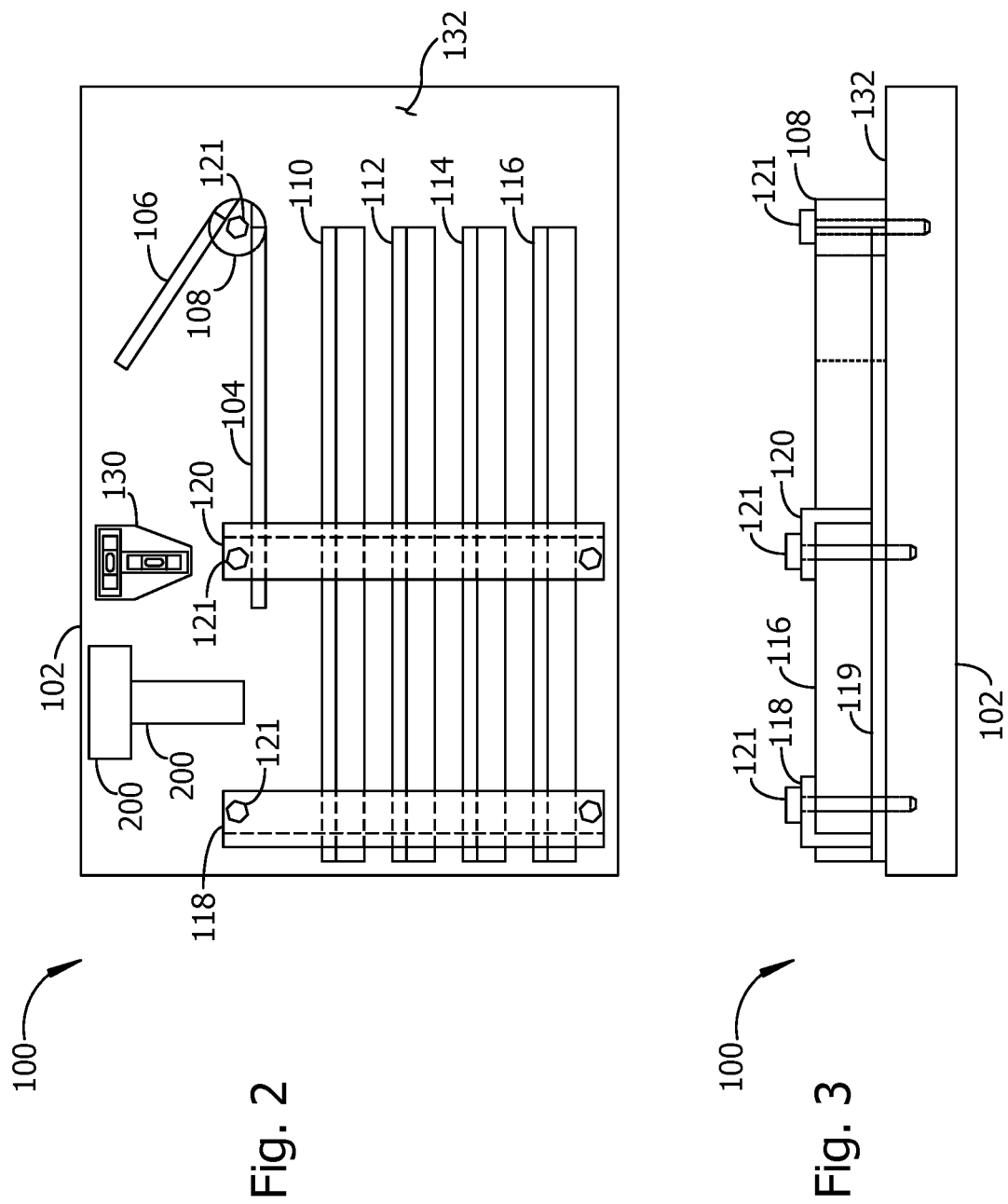

CALIBRATION OF AN INERTIAL MEASUREMENT UNIT FOR IMPROVING THE ACCURACY OF A BIOMECHANICAL SKELETON

FIELD OF THE INVENTION

Embodiments are generally related to calibration of sensors used for motion capture, and more particularly to calibration of sensors placed on a limb of a living subject whose movements are to be recorded by a motion capture system using an inertial measurement unit.

BACKGROUND

Motion capture of a living subject such as a person or animal may be performed by attaching an angle measurement device such as an inertial measurement unit (IMU) to a part of the subject's body and recording changes measured by the IMU in rotation values about one or more of the three mutually-perpendicular spatial axes as the subject moves about. The rotational data may be used to determine angular and linear positions of segments and joints in a biomechanical skeleton, a mathematical model of the subject's limb and joint positions.

It is common to assume that each of the spatial measurement axes of an IMU are parallel to the corresponding spatial axes of the corresponding biomechanical skeleton structure. For example, the IMU's X measurement axis may be assumed to be parallel to a longest axis of a limb segment of a biomechanical skeleton. However, when an IMU is attached to a motion capture subject, the IMU's measurement axes may be skew to the corresponding axes in the biomechanical skeleton. For example, an IMU placed on a subject's forearm may be tilted relative to the long axis of the limb by the contraction and relaxation of forearm muscles.

An angular offset between an actual IMU measurement of a motion capture subject and an IMU reference position on a biomechanical skeleton may lead to substantial position errors in calculated movements of the biomechanical skeleton. For example, an error in the rotational position of a living subject's hand compared to the position of the corresponding segment of the biomechanical skeleton may cause the hand on the biomechanical skeleton to pass through another solid object in a computer simulation of the subject's motions, or the hand may appear to grasp empty space near an object rather than making contact with the object. Similar errors may occur due to angular offsets in IMU values with other parts of a biomechanical skeleton compared to the subject's actual movements.

SUMMARY

An example of an apparatus embodiment includes a base plate having a top surface; an elongate index finger rest extending outward from the top surface; and an elongate thumb rest extending outward from the top surface, the thumb rest positioned to be interposed between a thumb and an index finger of a hand placed on the top surface. An optional fingertip bar may extend transversely across the plate.

The example apparatus embodiment may further include a partition coupling post attached to the index finger rest, the thumb rest, and the top surface.

The example apparatus embodiment may further include a first partition extending outward from the top surface, the first partition positioned to be interposed between the index finger and a middle finger of the hand. The example apparatus embodiment may further include a second partition extending outward from the top surface, the second partition positioned to be interposed between the middle finger and a ring finger of the hand.

The example apparatus embodiment may further include a fingertip bar positioned to hold the first partition against the top surface and to contact a fingertip on the hand.

The example apparatus embodiment may further include a third partition extending outward from the top surface, the third partition positioned to be interposed between the ring finger and a little finger on the hand, and with the third partition interposed between the fingertip bar and the top surface.

The example apparatus embodiment may further include a clamp bar extending transversely across the base plate with the first and second partitions interposed between the clamp bar and the top surface.

Another example embodiment includes any one or more of the following steps for using a calibration fixture:

on a dorsal surface of a hand, locating a first reference position adjacent a distal end of a metacarpal bone of an index finger;

locating a second reference position adjacent a distal end of a metacarpal bone of a middle finger on the hand;

locating a third reference position on a highest point in a carpal group of the hand, wherein the third reference position is proximal to the metacarpal bone of the index finger and the metacarpal bone of the middle finger; and positioning an inertial measurement unit (IMU) adjacent the dorsal surface of the hand, with the inertial measurement unit located within a perimeter of a triangle having a first vertex at the first reference position, a second vertex at the second reference position, and a third vertex at the third reference position.

BRIEF DESCRIPTION OF THE DRAWINGS

FIG. 2 is a view toward a top side of an example calibration fixture for a left hand.

FIG. 3 is a side view of the example calibration fixture of FIG. 2.

DESCRIPTION

A calibration fixture and method of use are described for measuring angular offsets between a measurement axis of an inertial measurement unit (IMU) and the corresponding reference plane used to determine positions of limbs and joints in a biomechanical skeleton. A calibration frame in accord with the disclosed embodiments holds a motion capture subject's hand in a controlled and accurately repeatable orientation, thereby enabling an accurate determination of offset angles between the measurement axes of the IMUs used for motion capture and the corresponding positions of limb segments and joints in a biomechanical skeleton used for computer modelling of the motion capture subject's movements.

The calibration fixture takes advantage of an observed physiological property of a human hand. When the palm of a hand is curled, for example by making a fist or by touching the tip of the thumb to the tip of the little finger, measurements with IMUs showed that a portion of the dorsal surface of the hand remains sufficiently invariant in shape and position to serve as an accurate position reference for a biomechanical model of the hand. The stable character of the identified part of the hand led to the development of a calibration fixture for determining an offset in a spatial angle between the body surface to which the IMU is attached and a horizontal reference plane used for defining an initial position of a biomechanical skeleton. After an IMU is calibrated on a fixture in accord with the disclosed embodiments, IMU motion capture data may be corrected by the determined spatial offset angle(s) and the angle of a surface of the calibration fixture to accurately position the corresponding biomechanical skeleton segment with respect to a selected reference plane.

Figure 1:
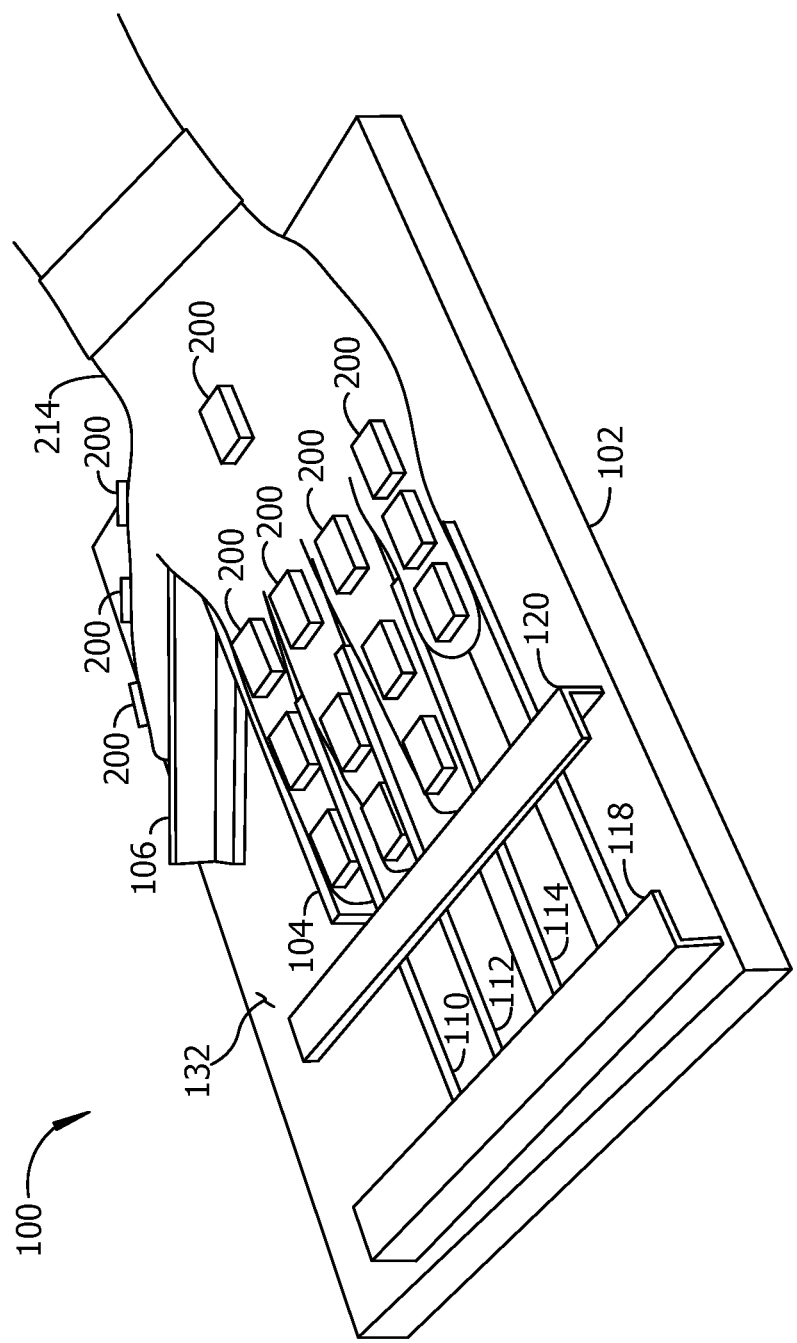
FIG. 1 is a pictorial view toward a top surface of an example calibration fixture.

FIG. 1 shows a pictorial view of an example calibration fixture embodiment. The example calibration fixture 100 includes a base plate 102 having a substantially flat top surface 132. In the illustrated example, a subject's hand inside a motion capture glove 214 is placed with the palm against the top surface 132, the index finger (digitus secundus manus) pressing against an elongate index finger rest 104 extending upward from the top surface of the base plate, and the thumb (pollex) pressing against an elongate thumb rest 106. The index finger rest 104 and thumb rest 106 may be separate parts joined by a coupling device as in the example of FIGS. 2-3 or may alternatively be formed as a single integral part.

The example calibration fixture 100 may optionally include any one or more of a first partition 110 positioned to be interposed between the index finger and middle finger (digitus medius) of the subject's hand, a second partition 112 positioned to be interposed between the middle finger and ring finger (digitus annularis), and a third partition 114 positioned to be interposed between the ring finger and the little finger (digitus minimus manus). The index finger rest 104 and thumb rest 106 provide a sufficiently repeatable position for the hand to allow accurate determination of an offset angle for a single IMU placed on the dorsal side of the hand opposite the palm. Additional partitions and rests (110, 112, 114, 116) may be provided to provide sufficiently repeatable positions for the fingers to allow accurate determine of offset angles for IMUs placed on the fingers.

As suggested in the example of FIG. 1, additional IMUs 200 may optionally be placed along the thumb and fingers to improve finger position accuracy compared to a model with a single IMU on the back of the palm. Each finger and thumb may have one or more of an IMU 200 positioned on a dorsal surface of the hand above a proximal phalange, an intermediate phalange, and a distal phalange. The disclosed embodiments are effective for measuring a separate value of angular offset for each IMU and applying the individual angular offset values to corresponding segments in a biomechanical skeleton.

FIGS. 2 and 3 show some additional features of an example calibration fixture 100. In the example calibration fixture 100 of FIGS. 2-3, an optional little finger rest 116 is provided to further restrain the position of the little finger relative to other parts of the hand. The thumb rest 106 and index finger rest 104 may be attached to a rounded post 108. The post 108 may be integrally formed with the top surface 132 of the base or may be attached by adhesive, welding, or a fastener 121. The post 108 provides a comfortable and accurately repeatable position for pressing the surface of the hand between the thumb and index finger against the fixture 100.

The position of the optional fingertip bar 120 may be adjustable to control a depth to which a subject's fingers are inserted between the partitions, thereby improving repeatability of calibration measurements. An optional little finger rest 116 may be positioned to further limit a position of the little finger of the hand when performing an IMU calibration. Alternatively, the fingertip bar 120 may be omitted and the partitions placed for contact with the skin between the proximal ends of adjacent fingers, thereby providing an accurately repeatable hand position on the fixture.

As suggested in FIGS. 2-3. the partitions (110, 112, 114, 116) may be held to the top surface 132 of the base 102 by the optional fingertip bar 120 and an optional clamp bar 118. The fingertip bar and clamp bar may be attached to the base plate 102 by fasteners 121. The partitions may be provided with a flange 119 to prevent the partitions from rocking side-to-side while being compressed by the clamp bar and fingertip bar.

In an alternative embodiment, the partitions (110, 112, 114, 116) and rests (104, 106) may be attached to the base 102 by passing through slots formed in the base with the upper parts of the partitions and rests extending outward from the top surface 132. A sufficiently close sliding fit between the partitions, rests, and slots in the base 102 may eliminate the need for fasteners 121 and may enable the calibration fixture 100 to be formed from low-cost plastic or fiberboard and shipped as a flat pack, to be assembled by the user.

A calibration fixture 100 may optionally include mutually perpendicular spirit levels, for example a T-level 130, to indicate when the top surface 132 of the calibration fixture is accurately horizontal and ready for determination of IMU offset angles. Alternatively, mutually perpendicular IMUs 200 may be attached to the top surface 132. The IMUs 200 may be connected to a measurement system (not shown) to give a visual and/or audible indication of the top surface 132 of the fixture 100 being level. The IMUs may optionally measure a tilt angle of the top surface 132, enabling the fixture to be used at any practical angle relative to the horizontal plane. An example of a suitable measurement system is shown in FIG. 14 of U.S. Patent Application Publication No. US 2015/0358543A1, incorporated herein by reference in its entirety.

The example calibration fixture 100 has been described for measuring offset angles with respect to a horizontal reference plane. When used with IMUs capable of measuring angles around more than one spatial axis, the calibration fixture 100 is equally effective for measuring offset angles with respect to a vertical reference plane by turning the fixture until the surface 132 is accurately vertical as indicated by the T-level 130 or IMUs 200 on the surface 132 of the fixture. As suggested previously, the calibration fixture may be used at any known tilt angle of the top surface 132, where the IMUs may be used to report the tilt angle of the surface.

Figure 4:
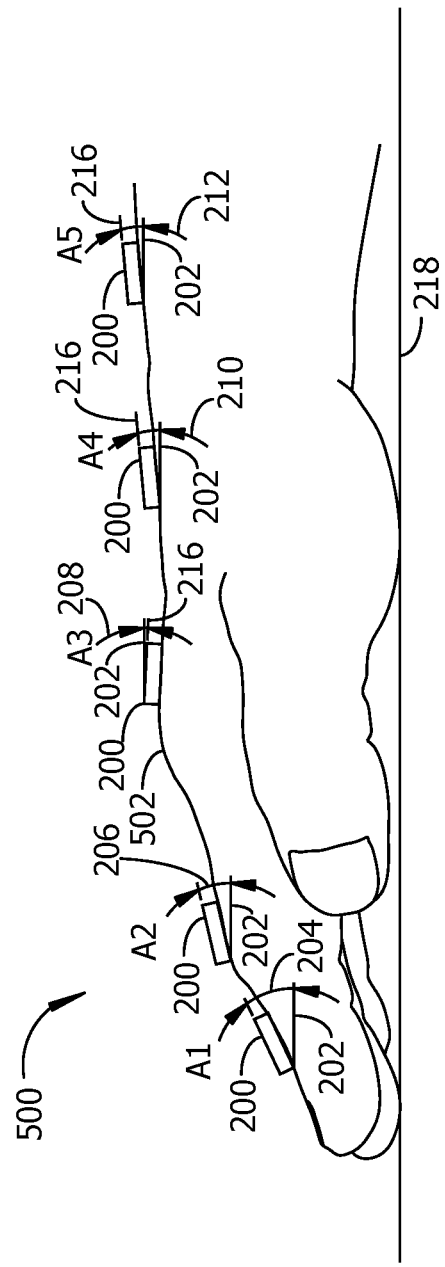
FIG. 4 is a side view of an example of a human right hand, showing examples of offset angles between IMU measurement axes and horizontal reference axes.

FIG. 4 shows several examples of offset angles to be determined by use of a calibration fixture 100. An example of a right hand 500 is shown with the palm flat against a horizontal reference surface 218. The outer surface 502 is generally nonparallel to the horizontal reference surface, so a measurement axis 216 of each IMU will also, in general, be nonparallel to the horizontal reference 218 and/or a local horizontal reference axis 202. The angular differences (A1, A2, A3, A4, A5) between the horizontal references and the measurement axis 216 of each IMU 200 correspond to the angular offset (204, 206, 208, 210, 212) for each IMU. The angular offsets may be algebraically positive or negative quantities. To accurately represent the position of the hand, the angular output data from each IMU is preferably corrected by that IMU's angular offset, as measured by the placement of the hand in the calibration fixture 100.

Figure 5:
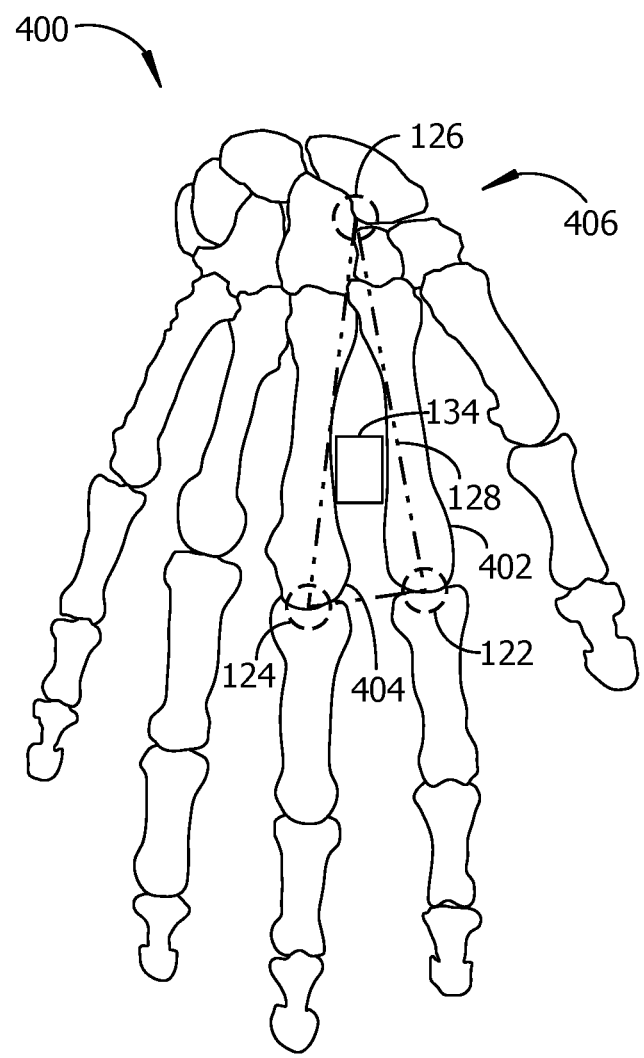
FIG. 5 is a view of the dorsal aspect of the bones of a human right hand, showing an example of a preferred IMU location for accurately modeling hand position with a biomechanical skeleton.

Measurements with IMUs have shown that a stable, repeatable reference region exists on the dorsal surface of a hand for representing the position and orientation of the palm portion of a hand in a biomechanical skeleton. FIG. 5 shows an example of the preferred stable reference region on a drawing of the bones 400 of a human right hand. The stable reference region is indicated by a reference triangle 128 drawn in broken lines. The vertices of the reference triangle 128 are the centers of circles at three readily identifiable and accurately repeatable locations on the back of the hand. The centers of the circles represent the positions on the dorsal exterior surface of the hand of the underlying physical structures used to define the reference triangle 128. A first reference position 122 for the first vertex of the reference triangle is positioned adjacent the distal end of the metacarpal 402 of the index finger. A second reference position 124 for the second vertex of the reference triangle is positioned adjacent the distal end of the metacarpal 404 of the middle finger. A third reference position 126 for the third vertex of the reference triangle 128 is positioned at a highest point felt through the skin in the carpal group 406, between the proximal ends of the metacarpals for the index and middle fingers and the wrist joint.

An IMU is preferably positioned adjacent the dorsal surface of the hand within the perimeter of the reference triangle 128, as shown in the example of FIG. 5 by a projected position 134 of an IMU within the broken-line perimeter of the reference triangle 128. The reference triangle 128 corresponds to a local, stable, repeatable definition of a reference plane for angular measurements by the IMU, when corrected for an offset angle between the IMU measurement axes and a horizontal reference plane. The same reference triangle 128 may be used to determine individual angular offsets for all of the IMUs coupled to one hand.

Figure 6:
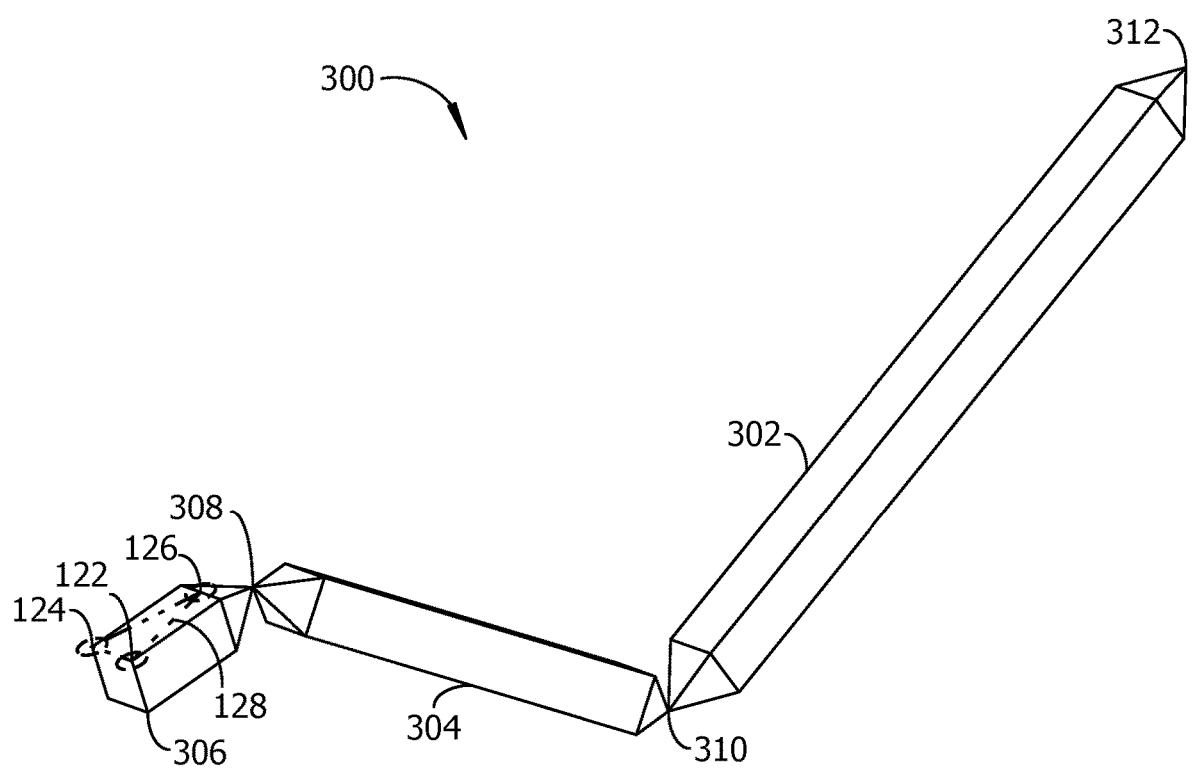
FIG. 6 is a pictorial view of an example biomechanical skeleton representing an upper arm, forearm, and hand for a person, showing an example of a reference plane used to accurately define a position of the hand segment of the model.

FIG. 6 shows an example biomechanical skeleton representing a human arm. The biomechanical skeleton 300 includes an upper arm segment 302 having a rotatable shoulder joint 312 at one end and rotatably coupled to a forearm segment 304 by an elbow joint 310 at the opposite end of the upper arm segment. The forearm segment 304 is rotatably coupled to a hand segment 306 through a rotatable wrist joint 308. An example position of the reference plane 128, represented by the reference triangle 128 with vertices (122, 124, 126), is shown in position on the hand segment 306. As suggested by the examples of FIG. 1 and FIG. 4, the hand segment 306 may be modified by adding IMUs to measure movements of individual fingers or segments of fingers.

Use of the example calibration fixture embodiments 100 may be described by the following steps:

on a dorsal surface of a hand, locating a first reference position adjacent a distal end of a metacarpal bone of an index finger;

locating a second reference position adjacent a distal end of a metacarpal bone of a middle finger on the hand;

locating a third reference position on a highest point in a carpal group of the hand, wherein the third reference position is proximal to the metacarpal bone of the index finger and the metacarpal bone of the middle finger; and positioning an IMU adjacent the dorsal surface of the hand, with the inertial measurement unit located within a perimeter of a triangle having a first vertex at the first reference position, a second vertex at the second reference position, and a third vertex at the third reference position.

The following steps may also be applied to use of the calibration fixture. The steps may be applied singly or in any combination or subcombination, and may be performed in a different order than shown here:

placing a palm of the hand against a top surface of a calibration fixture;

placing the index finger against an index finger rest on the calibration fixture;

placing a thumb of the hand against a thumb rest on the calibration fixture, with the thumb rest interposed between the index finger rest and the thumb;

measuring an offset angle of a measurement axis of the IMU relative to the top surface of the calibration fixture;

removing the hand from the calibration fixture;

measuring an angle of the hand with the IMU;

calculating a corrected angle of the hand, the corrected angle of the hand including an algebraic sum of the measured angle of the hand and the offset angle;

optionally, holding the top surface of the calibration fixture at a tilt angle between 0 degrees and 90 degrees to a horizontal plane, measuring the tilt angle to the horizontal plane with an IMYU on the fixture, and calculating corrected angles of the hand as the algebraic sum of the angle measured by the IMU, the offset angle determined by the calibration fixture for the IMU, and the tilt angle for the top surface of the calibration fixture.

determining a position of a segment in a biomechanical skeleton from the corrected IMU angle rather than the measured IMU angle;

optionally, holding the top surface of the calibration fixture parallel to a horizontal reference plane before measuring the offset angle of the IMU;

placing an index finger of the hand against the top surface and against an index finger rest on the calibration fixture;

placing a thumb of the hand against the top surface and against a thumb rest on the calibration fixture with the thumb rest interposed between the thumb and the index finger;

positioning a second IMU adjacent the dorsal surface of the hand along the metacarpal of the index finger;

measuring a second offset angle of a measurement axis of the second IMU relative to the top surface of the calibration fixture;

calculating a second corrected IMU angle for the second IMU as the algebraic sum of the second offset angle and another measured angle for the second IMU;

placing a middle finger of the hand against a second partition on the calibration fixture;

placing a ring finger of the hand against a third partition on the calibration fixture;

placing a little finger of the hand against a fourth partition on the calibration fixture;

placing an additional plurality of IMUs on the hand, wherein each additional IMU is positioned on a different segment of a finger from any other IMU;

for each additional IMU, measuring an offset angle;

for each additional IMU, calculating a corrected IMU angle from the offset angle for each IMU; and for each additional IMU, applying the corrected IMU angle to a corresponding segment of a biomechanical skeleton.

Unless expressly stated otherwise herein, ordinary terms have their corresponding ordinary meanings within the respective contexts of their presentations, and ordinary terms of art have their corresponding regular meanings.

What is claimed is:

1. An apparatus, comprising:

a base plate having a flat top surface;

a post affixed to said top surface;

an elongate index finger rest attached to said post, said index finger rest extending outward from said top surface, and said index finger rest in contact with said top surface everywhere along a longest dimension of said index finger rest;

an elongate thumb rest attached to said post, said thumb rest extending outward from said top surface, said thumb rest in contact with said top surface everywhere along a longest dimension of said thumb rest, said thumb rest positioned to be interposed between a thumb and an index finger of a hand placed on said top surface, and said post positioned to contact a surface of the hand between the index finger and the thumb;

a first partition positioned on said top surface adjacent said index finger rest;

a second partition positioned on said top surface adjacent said first partition;

a third partition positioned on said top surface adjacent said second partition;

a fourth partition positioned on said top surface adjacent said third partition;

a clamp bar attached to said base plate, said clamp bar in contact with said first partition, said second partition, said third partition, and said fourth partition, and not in contact with said index finger rest; and a fingertip bar attached to said base plate between said clamp bar and said post, said fingertip bar in contact with said first partition, said second partition, said third partition, said fourth partition, and said index finger rest;

wherein:

each of said first partition, second partition, third partition, and fourth partition comprise:

and end and an opposite end;

a flange having a bottom side in contact with said top surface, said bottom side of said flange extending above said top surface from said end to said opposite end;

a first side extending away from said flange and said top surface from said end to said opposite end, said flange extending away from said first side; and a second side opposite said first side, said second side extending away from said flange and said top surface, said second side extending from said end to said opposite end, and said second side parallel to said first side; and said index finger rest, said first partition, said second partition, said third partition, and said fourth partition positioned to receive a hand with an index finger of the hand against the index finger rest, said flange of said first partition interposed between a finger of the hand and said top surface, said flange of said second partition interposed between another finger of the hand and said top surface, and said flange of said third partition interposed between yet another finger of the hand and said top surface.

2. The apparatus of claim 1, said base plate formed without an aperture extending through said top surface and through a side of said base plate opposite said top surface.

3. The apparatus of claim 1, wherein said index finger rest and said thumb rest are positioned against said top surface without passing across an aperture through said base plate.

* * * * *